(12) United States Patent
Denawa et al.

(10) Patent No.: US 8,518,350 B2
(45) Date of Patent: Aug. 27, 2013

(54) REAGENT CONTAINER

(75) Inventors: Tatsuyuki Denawa, Kanagawa-ken (JP); Masayoshi Hayashi, Amagasaki (JP); Tatsuo Kurosawa, Amagasaki (JP); Masahiro Satomura, Amagasaki (JP); Mitsuo Watanabe, Amagasaki (JP)

(73) Assignee: Wako Pure Chemical Industries, Ltd., Hgoyo (JP)

( * ) Notice: Subject to any disclaimer, the term of this patent is extended or adjusted under 35 U.S.C. 154(b) by 127 days.

(21) Appl. No.: 12/680,093

(22) PCT Filed: Sep. 24, 2008

(86) PCT No.: PCT/JP2008/002641
§ 371 (c)(1),
(2), (4) Date: May 3, 2010

(87) PCT Pub. No.: WO2009/041031
PCT Pub. Date: Apr. 2, 2009

(65) Prior Publication Data
US 2010/0233035 A1    Sep. 16, 2010

(30) Foreign Application Priority Data

Sep. 25, 2007 (JP) ................. 2007-246617
Mar. 27, 2008 (JP) ................. 2008-083003

(51) Int. Cl.
*B01L 3/00* (2006.01)

(52) U.S. Cl.
USPC ........... 422/552; 422/547; 422/550; 422/553; 422/554

(58) Field of Classification Search
USPC ................. 422/547, 550, 551, 552, 553, 554
See application file for complete search history.

(56) References Cited

U.S. PATENT DOCUMENTS

| | | | |
|---|---|---|---|
| 3,676,076 A | 7/1972 | Grady | |
| 4,895,706 A * | 1/1990 | Root et al. | 422/534 |
| 5,297,599 A | 3/1994 | Bucheli | |
| 5,609,822 A | 3/1997 | Carey et al. | |
| 6,241,949 B1 * | 6/2001 | Kane | 422/553 |
| 2004/0067090 A1 | 4/2004 | Budds et al. | |
| 2007/0202010 A1 * | 8/2007 | Talebpour et al. | 422/61 |

FOREIGN PATENT DOCUMENTS

| | | |
|---|---|---|
| JP | 47-006740 A | 4/1972 |
| JP | 05-099931 A | 4/1993 |
| JP | 09-033535 A | 2/1997 |
| JP | 2002518680 A | 6/2002 |
| JP | 2004-156971 A | 6/2004 |
| JP | 2004-157020 A | 6/2004 |
| JP | 2004-518588 A | 6/2004 |
| JP | 2006-125978 A | 5/2006 |
| WO | 9966334 A1 | 12/1999 |

OTHER PUBLICATIONS

Japanese Office Action for Application No. 2008-083003; Oct. 9, 2012.

* cited by examiner

*Primary Examiner* — Jill Warden
*Assistant Examiner* — Dwayne K Handy
(74) *Attorney, Agent, or Firm* — Sughrue Mion, PLLC

(57) ABSTRACT

A reagent container having a plurality of open holding sections, each holding a reagent and into which a probe is inserted to suck the reagent. An opening of each of the holding sections is sealed with at least one sheet-like seal member. The reagent container includes a container body and a lid having a plurality of hollow piercing sections, formed on a lower surface of the lid, protruding downward for piercing the seal member at each of the openings, and openings, formed in an upper surface of the lid, communicating with piercing sections respectively to allow the probe to be inserted therethrough or withdrawn therefrom.

21 Claims, 12 Drawing Sheets

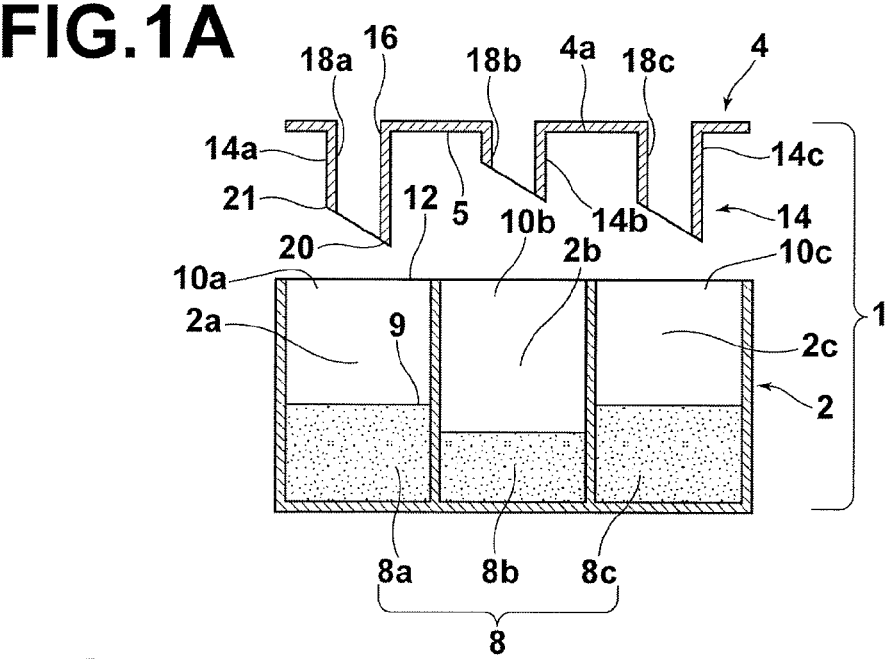
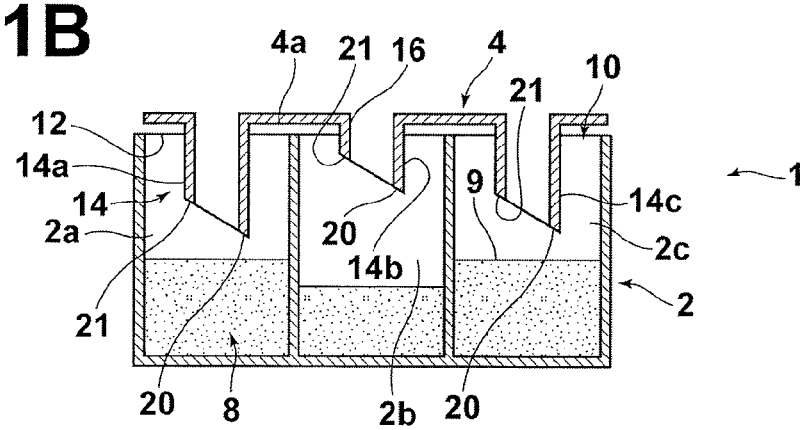
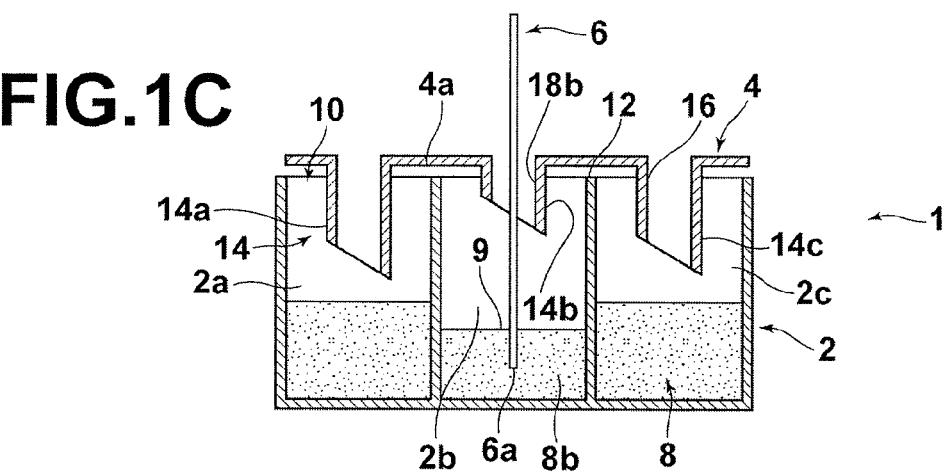

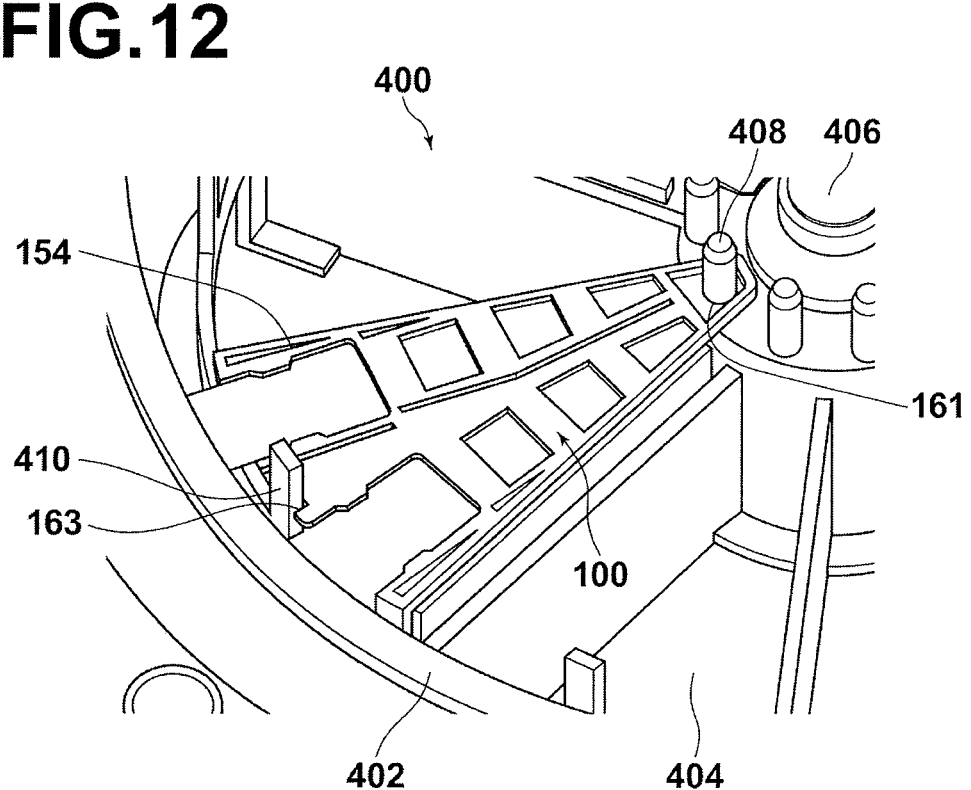

REAGENT CONTAINER

TECHNICAL FIELD

The present invention generally relates to a reagent container for use with an automatic analyzing device for analyzing, for example, a blood sample or the like, and more particularly to a reagent container for use with an automatic analyzing device that uses a dispensing probe (hereinafter, simply referred to as "probe") for sucking a small amount of a reagent from a reagent container and dispensing the reagent on a microchip or the like.

BACKGROUND ART

Microchips having a micro-channel are beginning to be used for automatic analyzing devices that analyze blood samples, urine samples, and the like. In such a microchip, a reagent, including a buffer (buffer fluid), is injected in a micro-channel by a probe and then a high voltage is applied to the micro-channel. The application of the high voltage causes each composition component of the sample in the channel to be migrated, and a target substance for measurement in the sample is separated by the difference in the degree of migration. The target substance separated is identified by the reagent and detected in a detection section of the analyzing device. A series of these processes is performed automatically in the analyzing device.

In the mean time, it is often the case that one analyzing item, for example, the analysis of a particular protein requires a plurality of different reagents. These reagents are provided in reagent containers in advance, and a plurality of reagent containers is disposed in an analyzing device. Under the circumstances described above, it is desired that analyzing devices may include therein many reagent containers by downsizing the containers for efficient analysis. A typical reagent container has an opening for inserting a probe, but the opening is normally covered with a screw cap to seal the inside. When using such type of reagent container, the cap is manually removed and then the reagent is mounted in an analyzing device.

Further, a method of piercing a screw cap by a pipette for sucking a reagent without manually removing the screw cap is also known as described, for example, in Japanese Unexamined Patent Publication No. 5 (1993)-099931. In the conventional method described in the aforementioned patent document, a pipette is inserted into a reagent container by pushing open the tip (bottom) of an inverted conically shaped cap with the tip of the pipette moved downward. When the pipette is pulled out from the reagent container, the reagent adhered to the tip of the pipette is wiped out by the edge portion of the hole pierced in the tip of the cap.

Further, another type of conventional reagent container in which a lid having a hinge mechanism is provided on the opening of the container is also known as described, for example, in Japanese Unexamined Patent Publication No. 2004-156971. Such a reagent container is designed, after being mounted in an analyzing device, to automatically open/close the lid by the hinge mechanism in cooperation with a mechanism provided in the analyzing device.

In the typical reagent container having a screw cap described above, the cap size is greater than the opening size of the reagent container so that it has been difficult to closely pack a plurality of reagent holding sections in one reagent container. Further, even when the amount of a reagent to be held is very small, it has been difficult to downsize the reagent container because of a limitation in downsizing the cap. Further, it has been necessary to individually open the caps one by one, requiring the time and effort if there are many caps to be opened. Still further, it has been difficult for a reagent container holding a plurality of types of reagents to hold the reagents in a balanced manner in which, depending on the type of reagents, volume of reagent decreases when required amount is small and volume of reagent increases when required amount is large.

In the reagent container described in Japanese Unexamined Patent Publication No. 5 (1993)-099931, a sufficient strength is required for the pipette to pierce a synthetic resin cap. It is difficult, however, to expect the pipette to have a sufficient strength to pierce the cap because the pipette is used for accurately handling a minuscule amount of a liquid reagent and therefore needs to be as thin as possible in order to reduce the adherence of the reagent other than the amount to be sucked. Further, when the pipette is pulled out of the cap after sucking a reagent, the pipette is wiped by the pierced hole so that the liquid is adhered around the hole in the cap. The adherence of the liquid to the cap may lead to an erroneous detection of the liquid level of the reagent when detected by a capacitance measurement. That is, there may be a case in which the pipette would have been erroneously judged to reach the liquid level when the pipette contacted the liquid around the hole, causing it difficult to perform accurate liquid level detection repeatedly. Further, the reagent adheres to a portion of the pipette other than the tip when the pipette passes through the pierced hole of the cap adhered with the liquid, whereby the pipette is contaminated with the reagent to an upper portion of the tip that actually contacts the liquid level of the reagent. Generally, the tip of a pipette is cleaned with water or the like each time the sucking is performed to reduce the residual amount of the reagent to a predetermined amount, if a larger pipette portion contacts the liquid, the more area needs to be cleaned, posing a problem that more time and effort is required for the maintenance.

In the reagent container disclosed in Japanese Unexamined Patent Publication No. 2004-156971, it is difficult to closely pack a plurality of reagent holding sections in one reagent container because the container needs to be provided with a bulky hinge mechanism. In addition, a mechanism for opening/closing the hinge mechanism needs to be provided in the analyzing device, resulting in that the analyzing device becomes complicated in structure and expensive.

The present invention has been developed in view of the circumstances described above, and it is an object of the present invention to provide a reagent container capable of holding a plurality of reagents therein and yet reduced size.

It is a further object of the present invention to provide a reagent container that allows easy opening, i.e., easy piercing.

It is another object of the present invention to provide a reagent container that does not require a strong probe.

It is still another object of the present invention to provide a reagent container capable of reducing contamination of a probe and the like by a sample.

It is a further object of the present invention to provide a reagent container that constantly allows accurate liquid level detection by a general capacitance measurement.

DISCLOSURE OF THE INVENTION

A reagent container of the present invention is a container including: a container body having a plurality of open holding sections, each holding a reagent and into which a probe of an automatic analyzing device is inserted to suck the reagent, with an opening of each of the holding sections sealed with at least one sheet-like seal member; and a lid having a plurality of hollow piercing sections, formed on a lower surface of the lid, protruding downward for piercing the seal member at each of the openings, and openings, formed in an upper surface of the lid, communicating with piercing sections respectively to allow the probe to be inserted therethrough or withdrawn therefrom, wherein the reagent container is configured such that the seal member is pierced by pressing the lid onto the container body from above and the probe is allowed to be inserted into the holding sections through hollow sections of the piercing sections.

The reagents may include a plurality of types of reagents and each of the holding sections may hold an amount of each of the corresponding reagents according to a required amount thereof.

Further, at least one of the openings of the plurality of holding sections may have a size different from the size of the rest of the openings and each of the piercing sections may have the same outer dimension.

Preferably, the seal member is made of a material that adheres tightly to the piercing sections of the lid after pierced.

It is also preferable that the seal member is made of a material that does not produce a fragment separated from the seal member when piercing is performed by the piercing sections.

Preferably, at least one of the plurality of piercing sections has a protruding length protruding downward from the lower surface of the lid different from the protruding length of the rest of the piercing sections, whereby the piercing sections are configured to pierce the seal member in a stepwise manner.

Further, a handle may be provided on the outside of the reagent container.

Still further, the lid may include an engaging section that engages with the container body to hold the lid at a position above the container body where the piercing sections do not interfere with the seal member.

Further, the container body may be shaped like a block having an outer circumferential wall, and the lid may include a cover wall whose inner wall surface is guided by the outer circumferential wall when the lid is pressed onto the container body from above and an upper wall having the piercing sections on a lower surface thereof.

Still further, the lid may include a positioning section that engages with a member on the side of the automatic analyzing device so as to be fixedly positioned.

Preferably, at least one of the piercing sections is disposed at a position where a shortest distance from an inner wall surface of the corresponding opening of the container body to an outer circumferential surface of the piercing section is not greater than ½ of a shortest distance from the inner wall surface to the center of the piercing section.

It is also preferable that at least one of the openings of the container body has a similar shape portion along an outer circumferential surface of the corresponding piercing section and the length of the similar shape portion along the outer circumferential surface is not less than 25% of the length of the outer circumferential surface.

The reagent container of the present invention includes a container body with an opening of each of the holding sections sealed with at least one sheet-like seal member and a lid having a plurality of hollow piercing sections formed on a lower surface thereof to protrude downward and openings formed in an upper surface thereof to allow the probe to be inserted therethrough or withdrawn therefrom, and the container is configured such that the seal member is pierced by pressing the lid onto the container body from above and the probe is allowed to be inserted into the holding sections through the hollow sections of the piercing sections. Therefore, reagent container of the present invention has the following advantageous effects. That is, normally, the openings of the container body are only sealed with the seal member so that it is not bulky and the container body is simply covered with the lid, and so that the reagent container can be made small even if it has a plurality of holding sections. Further, piercing of the container body can be made at a time by simply pressing the lid onto the container body, so that the piercing of the container body is extremely easy. Further, the hollow piercing sections secure the passage of the probe so that the probe does not require a specific strength and a required thinness may be ensured, and contamination of a portion of the probe other than the tip thereof may be prevented. Still further, this ensures accurate liquid level detection even by a capacitive method.

When the reagents include a plurality of types of reagents and each of the holding sections is configured to hold an amount of each corresponding reagent according to a required amount thereof, the reagent container may be made small in which the plurality of types of reagents is held in a balanced manner according to the required amount of each type of reagent.

Further, when at least one of the openings of the plurality of holding sections has a size different from the size of the rest of the openings and each of the piercing sections has the same outer dimension, the force required for each piercing section for performing piercing becomes substantially uniform, whereby the piercing may be performed stably.

Still further, when the seal member is made of a material that adheres tightly to the piercing sections of the lid after pierced, the reagents are shut off from the external environment so that leakage of the reagents may be prevented and a quality change or a concentration change due to evaporation in the reagents may be prevented, whereby measurement results are prevented from being affected by such changes.

Further, when the seal member is made of a material that does not produce a fragment separated from the seal member when piercing is performed by the piercing sections, dropping of a fragment of the seal member into a holding section is prevented and the probe is prevented from being adversely affected by the fragment dropped in the holding section.

Preferably, the seal member is a member that allows a hole having a shape identical to the cross-section of the outer circumference of the piercing section to be formed.

Further, when at least one of the plurality of piercing sections has a protruding length protruding downward from the lower surface of the lid different from the protruding length of the rest of the piercing sections, whereby the piercing sections are configured to pierce the seal member in a stepwise manner, an intensive force is not required for the piercing but the required force can be dispersed so that the piercing operation can be performed with a less amount of force.

Still further, when a handle is provided on the outside of the reagent container, the handling of the reagent container becomes easy.

Further, when the lid includes an engaging section that engages with the container body to hold the lid at a position above the container body where the piercing sections do not interfere with the seal member, the reagent container can be handled and carried effectively with the lid and container body being engaged with each other.

Still further, when the container body is shaped like a block having an outer circumferential wall, and the lid includes a cover wall whose inner wall surface is guided by the outer circumferential wall when the lid is pressed onto the container body from above and an upper wall having the piercing sections on a lower surface thereof, the inner wall surface of the lid is guided by the outer circumferential wall. Therefore, the opening, i.e., piercing of the reagent container may be made easily and stably.

Further, when the lid includes a positioning section that engages with a member on the side of the automatic analyzing device so as to be fixedly positioned, the probe of the automatic analyzing device and the opening of the piercing section of the lid into which the probe is inserted are aligned reliably. Therefore, the probe is prevented from damage or contamination due to contact of the probe with the lid.

Still further, when at least one of the piercing sections is disposed at a position where a shortest distance from an inner wall surface of the corresponding opening of the container body to an outer circumferential surface of the piercing section is not greater than ½ of a shortest distance from the inner wall surface to the center of the piercing section, the piercing becomes easy by minimizing the deflection of the seal member and the repeatability of the piercing may be improved reliably.

Further, when at least one of the openings of the container body has a similar shape portion along an outer circumferential surface of the corresponding piercing section and the length of the similar shape portion along the outer circumferential surface is not less than 25% of the length of the outer circumferential surface, the piercing becomes more easily by further minimizing the deflection of the seal member and the repeatability of the piercing may be further improved combined with the fact that at least one of the openings of the container body has a similar shape portion along an outer circumferential surface of the corresponding piercing section.

BRIEF DESCRIPTION OF THE DRAWINGS

FIG. 1A is a conceptual cross-sectional view of a reagent container of the present invention, illustrating a container body constituting the reagent container and a lid as a piercing member located upper side of the container body.

FIG. 1B is a conceptual cross-sectional view of the reagent container of the present invention, illustrating the state in which the lid is pressed onto the container body and a seal member is pierced.

FIG. 1C is a conceptual cross-sectional view of the reagent container of the present invention, illustrating the state in which a dispensing probe is inserted into the reagent container through the lid.

FIG. 12 is a perspective view in which the reagent container according to the third embodiment is mounted in an automatic analyzing device.

BEST MODE FOR CARRYING OUT THE INVENTION

Figure 2:
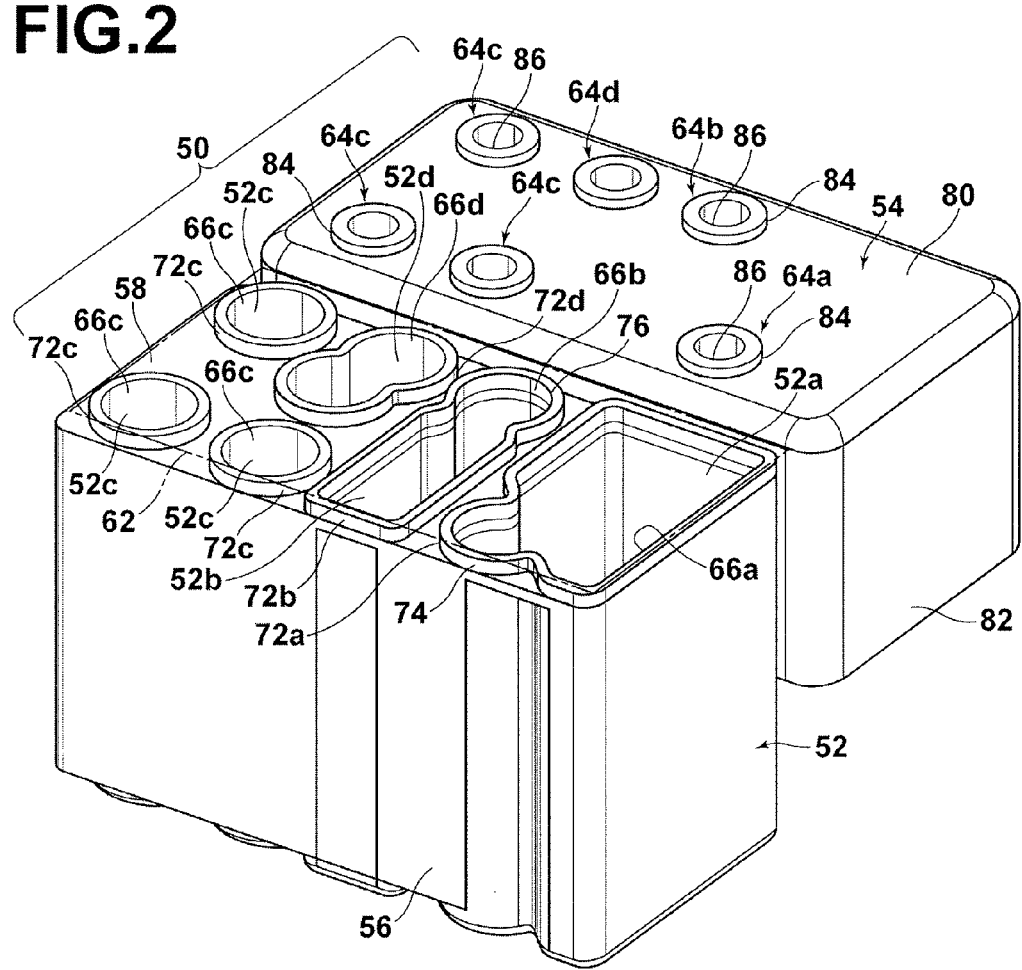
FIG. 2 is a perspective view of a reagent container according to a first embodiment of the present invention, illustrating the container body and lid separately.

Hereinafter, an example reagent container of the present invention will be described in detail with reference to the accompanying drawings. FIGS. 1A, 1B, and 1C are conceptual cross-sectional views of a reagent container of the present invention. FIG. 1A illustrates container body 2 constituting reagent container 1 and lid 4 as a piercing member located on the upper side of the container body. FIG. 1B illustrates the state in which lid 4 is pressed onto container body 2 and a seal member is pierced. FIG. 1C illustrates the state in which dispensing probe (hereinafter, simply referred to as "probe") 6 is inserted into reagent container 1 through lid 4.

As shown in FIGS. 1A to 1C, container body 2 has a plurality of holding sections 2a, 2b, and 2c open at the upper side. These cross-sectional views indicate three holding sections 2a, 2b, and 2c, but the holding section is not limited to three. Holding sections 2a, 2b, and 2c hold different types of reagents 8a, 8b, and 8c respectively. Normally, holding sections 2a, 2b, and 2c have volumes according to required amounts of reagents respectively, but they may have the same volume. Reagents 8a, 8b, and 8c are, hereinafter, collectively referred to as reagents 8.

Opening sections 10a, 10b, and 10c of respective holding sections 2a, 2b, and 2c are sealed with one sheet-like seal member 12. Seal member 12 shown in FIGS. 1A to 1C is a continuous seal member, but opening sections 10a, 10b, and 10c may be sealed with separate seal members (not shown). Opening sections 10a, 10b, and 10c are, hereinafter, collectively referred to as opening sections 10. Since container body 2 is sealed with seal member 12, leakage of reagent 8 during transportation is prevented so that the reagent container can be handled with ease. The material of the seal member may be a thin film, such as an aluminum foil. The seal member may have a layer structure in which an aluminum foil is laminated with a resin, such as a polypropylene, on either one of the sides or on each side.

Lid 4 includes main body 4a extending so as to cover the upper face of container body 2 and cylindrical piercing sections 14a, 14b, and 14c. And they are integrally formed with, for example, a synthetic resin. In the conceptual views of FIGS. 1A to 1C, the size of main body 4a of lid 4 in a horizontal direction is substantially the same as the size of container body 2 in the horizontal direction. Piercing sections 14a, 14b, and 14c are, hereinafter, collectively referred to as piercing sections 14. Piercing sections 14a, 14b, and 14c are formed at positions corresponding to opening sections 10a, 10b, and 10c respectively so as to protrude perpendicularly to lower surface 5 of main body 4a. And the outer diameters of piercing sections 14a, 14b, and 14c are the same.

Each of piercing sections 14a, 14b, and 14c may have a cylindrical shape or rectangular or other shapes in cross-section. The lower end of piercing section 14 has a shear angle, i.e., the lower end is cut obliquely and tip 20 has a sharp shape. Further, each of piercing sections 14a, 14b, and 14c has each of hollow passages (hollow sections) 18a, 18b, and 18c communicating with opening 16 of main body 4a. The inner diameter of each of passages 18a, 18b, and 18c is sufficiently large for probe 6 to pass therethrough without touching. Passages 18a, 18b, and 18c are, hereinafter, collectively referred to as passages 18. Passages 18 may have any shape in cross-section, such as a circular shape, an appropriate polygonal shape, or the like as long as it is capable of receiving probe 6. The tip shape of piercing sections 14 is not limited to the shape linearly cut obliquely, and may have any shape, such as a V shape, an inverted V shape, or a combination thereof. In any shape, it is preferable that the tip is sharp enough to pierce seal member 12.

In the conceptual views in FIGS. 1A to 1C, piercing section 14a and piercing section 14c have substantially the same length, while piercing section 14b has a shorter length than that. The reason is, when pressing lid 4 onto seal member 12 to push open holes, to prevent the concentration of force required for piercing the holes by causing the piercing sections to contact and pierce seal member 12 in a stepwise manner. Accordingly, piercing sections 14a, 14b, and 14c may have lengths different from each other for this purpose. Where lid 4 has a large number of piercing sections 14, the sections may be grouped and the protruding length may be changed with respect to each group. For example, if there are seven piercing sections 14, then they may be divided into two groups of three and four sections. If the piercing requires a small force, then all piercing sections 14a, 14b, and 14c may have the same length.

Then, as shown in FIG. 1B, when lid 4 is pressed down toward container body 2, seal member 12 is pushed and broken by tips 20 of piercing sections 14, whereby holes are pierced. That is, piercing sections 14 pass through seal member 12. When the piercing is performed, seal member 12 is prevented from being broken into fragments and dropping into reagents 8 because seal member 12 is made of one of the materials described above. Further, edge portions of pierced seal member 12 adhere tightly to the outer circumferential surfaces of piercing sections 14. As described above, the protruding length of piercing sections 14a and 14c is different from that of piercing section 14b. Therefore, seal member 12 is pushed open first by piercing sections 14a and 14c and then by piercing section 14b. This stepwise piercing requires a less amount of force for lid 4 to push open seal member 12. This piercing causes holding sections 2a, 2b, and 2c to be communicated with the outside through passages 18a, 18b, and 18c respectively. In this way, the plurality of holding sections 2a, 2b, and 2c of container body 2 is pierced, i.e., opened collectively by a single operation of pressing down lid 4.

Thereafter, reagents 8 are sucked from reagent container 1. As shown in FIG. 1C, probe 6 of an analyzing device is moved down, for example, to holding section 2b through opening 16 and passage 18b. When detection is made that the tip 6a of probe 6 has reached reagent 8b by, for example, a capacitive liquid level detector (not shown), reagent 8b is automatically sucked by probe 6. When probe 6 is inserted into holding section 2b, there is no possibility that probe 6 contacts piercing section 14b since passage 18b is provided. The same is true for holding sections 2a and 2c.

Preferably, seal member 12 is made of a material, such as a laminated aluminum foil that does not drop into holding sections 2a, 2b, and 2c in fragments as described above. It is also preferable that, after seal member 12 is pushed and broken by piercing sections 14 (14a, 14b, 14c), the broken edges adhere tightly to the outer circumferential surfaces of piercing sections 14 (14a, 14b, 14c) without blocking passages 18 of piercing sections 14 (14a, 14b, 14c). This may prevent probe 6 from contacting seal member 12 and reagents 8a, 8b, and 8c from adhering to seal member 12.

If a portion of seal member 12 pushed and broken by piercing sections 14 is present in a position blocking passages 18, though partially, reagents 8 may possibly adhere to seal member 12 by the insertion and extraction of probe 6 passing through passages 18. Adhesion of reagents 8 may possibly cause a portion of probe 6 other than the tip 6a is contaminated by reagents 8. Further, this may possibly cause erroneous detection of liquid levels 9 of reagents 8. That is, in the case of using capacitive liquid level detection method, contact of probe 6 with reagents 8 of seal member 12 may possibly be judged that tip 6a of probe 6 has reached liquid levels 9 of reagents 8.

In this respect, piercing sections 14 should have certain lengths with respect to punching diameter, i.e., the diameter of pierced holes. More specifically, it is preferable that the lengths of piercing sections 14, i.e., the lengths from lower surface 5 of main body 4a of lid 4 to ends 21 which are shorter in protruding length than tips 20, are not less than 80%, more preferably not less than 90%, and the most preferably not less than 100% of the punching diameter. In this case, however, the lengths of tips 20 should be a length that does not reach liquid levels 9 of reagents 8 after piercing.

Figure 3:
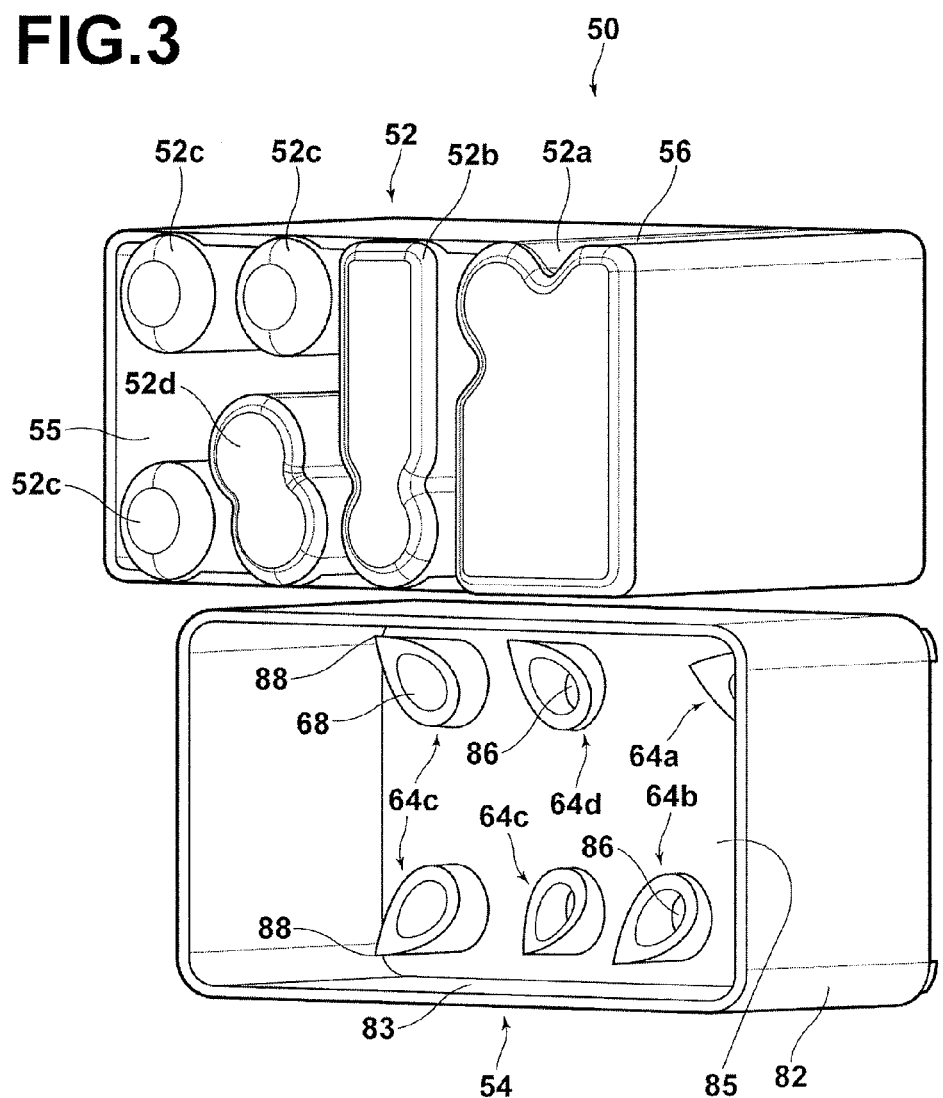
FIG. 3 is a perspective view of the reagent container shown in FIG. 2 viewed from below.

A first embodiment of the reagent container based on the concepts described above will now be described with reference to FIGS. 2 and 3. In FIGS. 2 and 3, components identical to those shown in conceptual drawings of FIGS. 1A to 1C are given the same reference numerals. FIG. 2 is a perspective view of reagent container 50 according to a first embodiment, illustrating container body 52 and lid 54 separately. FIG. 3 is a perspective view of reagent container 50 shown in FIG. 2 viewed from below. As shown in FIGS. 2 and 3, container body 52 has a box- (block-) like outer shape integrally formed, for example, with a synthetic resin, and includes frame-like outer circumferential wall 56 having internal space 55 (FIG. 3) and top wall 58 (FIG. 2). Top wall 58 has a plurality of holding sections 52a, 52b, 52c, and 52d, each holding reagent 8, integrally formed with top wall 58 to hang down perpendicularly in the internal space 55. Holding section 52a has a cuboid shape formed so as to include a portion of outer circumferential wall 56, holding section 52c has a cylindrical shape, and holding section 52d has a tubular shape with a gourd shape or an outer shape of two intersected circles in cross-section. Holding section 52b located between holding sections 52c, 52d and holding section 52a has substantially a cuboid shape smaller than holding section 52a.

Holding sections 52a, 52b, 52c, and 52d have openings (opening sections) 66a, 66b, 66c, and 66d respectively (FIG. 2). Openings 66a, 66b, 66c, and 66d are, hereinafter, collectively referred to as openings 66. Opening 66a has curved opening 74 at one of the four corners (FIG. 2). Also opening 66b has curved opening 76 at one end (FIG. 2). Curved openings 74, 76 have curved surfaces substantially concentric with cylindrical outer circumferential surfaces of piercing sections 64.

Ribs 72a, 72b, 72c, and 72d enclosing openings 66a, 66b, 66c, and 66d respectively are provided protrudingly from top wall 58 around openings 66a, 66b, 66c, and 66d. Ribs 72a, 72b, 72c, and 72d are, hereinafter, collectively referred to as ribs 72. Ribs 72 can prevent ingress of water drops. That is, when reagent container 50 is placed under a low temperature environment like in reagent storage of an analyzing device, water drops may possibly adhere to top wall 58. In such a case, the water drops can be prevented from entering holding sections 52a, 52b, 52c, and 52d by ribs 72. One seal member 62 (FIG. 2) identical to seal member 12 is bonded to Ribs 72a, 72b, 72c, and 72d, for example, by ultrasonic welding in order to prevent reagents held in holding sections 52a, 52b, 52c, and 52d from leaking. Openings 66a, 66b, 66c, and 66d of holding sections 52a, 52b, 52c, and 52d may be sealed with separate seal members (not shown), instead of one seal member 62.

Next, lid 54 will be described. Lid 54 has a cuboid shape formed by upper wall 80 (FIG. 2) of a size covering top wall 58 of container body 52 and cover wall 82 of a size to be fitted by outer circumferential wall 56 of container body 52. Upper wall 80 and cover wall 82 are integrally formed, for example, with a synthetic resin, and the space enclosed by cover wall 82 is open at the lower side. Piercing sections 64 (64a, 64b, 64c, and 64d) having hollow passages 68 (FIG. 3) are formed at positions of upper wall 80 corresponding to openings 66a, 66b, 66c, and 66d of holding sections 52a, 52b, 52c, and 52d of container body 52. Piercing sections 64a, 64b, 64c, and 64d have the same outer in a planar view. As shown in FIG. 2, annular ribs 84 enclosing openings 86 (FIG. 2) are provided protrudingly from upper wall 80. Ribs 84 may prevent water drops from entering openings 84 like ribs 72 described above.

As shown in FIG. 3, piercing sections 64 (64a, 64b, 64c, and 64d) protrude downward in the space defined by inner wall surface 83 from lower surface 85 of upper wall 80. Lower ends of piercing sections 64 (64a, 64b, 64c, and 64d) are inclined, like chopped off, and tips 88 protrude sharply so as to pass through seal member 62 easily. The lengths of piercing sections 64 (64a, 64b, 64c, and 64d), i.e., protruding lengths thereof are different, for example, between adjacent piercing sections 64c and 64d. When using lid 54, lid 54 is put on container body 52 from above and pressed downward to pass piercing section 64 (64a, 64b, 64c, and 64d) through seal member 62. Seal member 62 and piercing section 64 (64a, 64b, 64c, and 64d) are brought into close contact with each other, so that lid 54 is held on container body 52. Thereafter, reagent container 50 is mounted in an analyzing device, and probe 6 (FIG. 1C) is inserted from openings 86.

A reagent container having a cuboid outer shape, like reagent container 50, is suitable for mounting in parallel in an analyzing device. Further, if tips 88 of piercing sections 64 are oriented to the side of cover wall 82, i.e., the outer side in directions orthogonal to a longitudinal direction of lid 54 (oriented opposite to each other), the area of lid 54 supported by seal member 62 becomes wider when lid 54 is pressed onto seal member 62, whereby lid 54 may be pressed onto container body 52 stably.

Figure 4A:
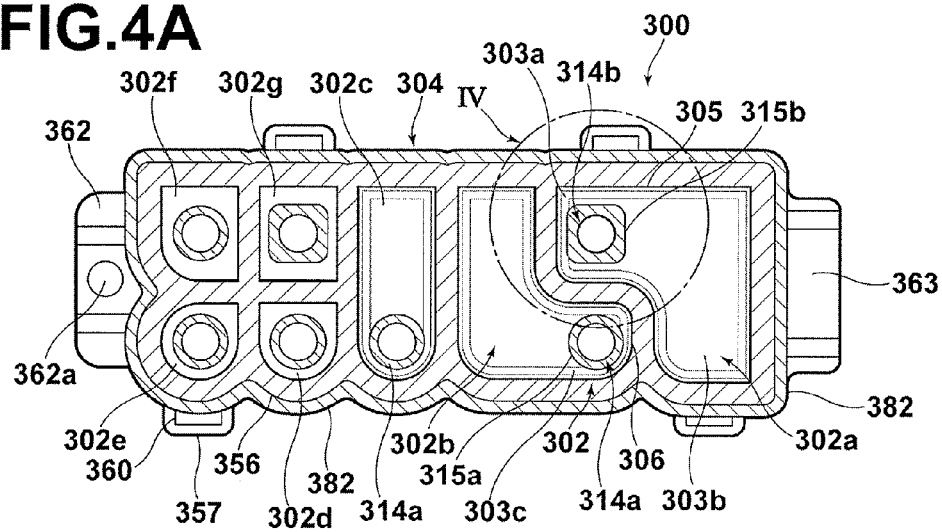
FIG. 4A is a cross-sectional view of a reagent container according to a second embodiment of the present invention taken along a horizontal plane.
Figure 4B:
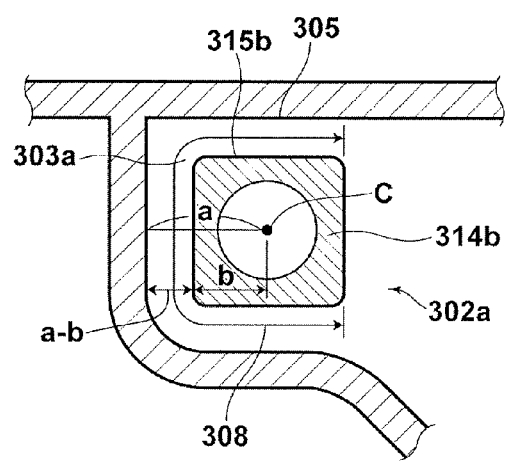
FIG. 4B is an enlarged view of the relevant part of the reagent container according to the second embodiment of the present invention within the circle indicated by IV in FIG. 4A.
Figure 4C:
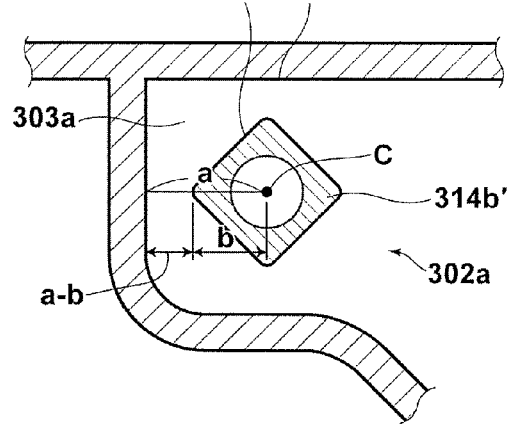
FIG. 4C is a cross-sectional view of the reagent container according to the second embodiment of the present invention in which a piercing section is formed rotated by 45° with respect to the piercing section shown in FIG. 4A.

Next, a reagent container according to a second embodiment of the present invention will be described with reference to FIGS. 4A, 4B, and 4C. FIG. 4A is a cross-sectional view of reagent container 300 according to the second embodiment taken along a horizontal plane. FIG. 4B is an enlarged view of the relevant part within the circle indicated by IV in FIG. 4A. FIG. 4C is a cross-sectional view of a reagent container in which a piercing section is formed rotated by 45° with respect to the piercing section shown in FIG. 4A. As shown in FIG. 4A, reagent container 300 includes a substantially block-like container body 302 and lid 304 fitted by container body 302. Container body 302 has holding sections 302a, 302b, 302c, 302d, 302e, 302f, and 302g. Holding sections 302a, 302b, 302c, 302d, 302e, 302f, and 302g differ in cross-sectional shape from each other. In FIG. 4A, a circular portion and a rectangular portion shown in holding sections 302a, 302b, 302c, 302d, 302e, 302f, and 302g are piercing sections 314 (314a and 314b) of lid 304. Piercing section 314a has a cylindrical shape and piercing section 314b has a square tubular shape. Piercing sections 314a and 314b have outer circumferential surfaces 315a and 315b respectively.

Piercing sections 314a, 314b, and 314c located in holding sections 302a, 302b, and 302c are located in corners of corresponding holding sections 302a, 302b, and 302c. The reason is that, in general, the seal member can be sheared more easily if the inner wall surface and the outer circumferential surface of the piercing section are in more close proximity. In this case, it is preferable that a piercing section is disposed at a position where a shortest distance from an inner wall surface of the opening section to the outer circumferential surface of the piercing section is ½, and more preferably ⅓ of the shortest distance from the inner wall surface to the center of the piercing section. On the other hand, if the piercing section should be located in the center of the holding section, the piercing position would become remote from the inner wall surface of the holding section and a seal member, not shown, would tend to bend down, causing the piercing difficult. Further, with respect to holding section 302a, it has a rectangular shape with a missing corner in cross-section and includes two concave portions 303a and 303b. Piercing section 314b is located in concave portion 303a such that outer circumferential surface 315b of piercing section 314b is substantially parallel with inner wall surface 305 of the opening of holding section 302a. In other words, a portion of inner wall surface 305 is in a similarity relationship with outer circumferential surface 315b of piercing section 314b. This brings inner wall surface 305 and outer circumferential surface 315b of piercing section 314b closer to each other, and seal member 12 can be sheared more easily. As shown in FIG. 4C, assuming the center of piercing section 314b' to be "c", if the distance (a-b) from inner wall surface 305 to outer circumferential surface 315b' of piercing section 314b' is small, the disposition in a similarity relationship is not necessarily required but is preferable. Further, if the inner wall surface and outer circumferential surface are in close vicinity to each other, for example, a combination of a circular piercing section and a rectangular inner wall surface, a combination of a rectangular piercing section and a circular inner wall surface, or the like may be employed.

The same applies to piercing section 314a in holding section 302b. That is, circular piercing section 314a is disposed inside of curved inner wall surface 306 in concave portion 303c of holding section 302b. That is, a portion of curved inner wall surface 306 is in a similarity relationship with outer circumferential surface 315b of cylindrical piercing section 314a. The similarity relationships between inner surface walls 305 and 306, and piercing sections 314b and 314a respectively will be described in more detail with reference to FIG. 4B.

A portion of inner wall surface 305 at concave portion 303a of holding section 302a which is similar to the shape of outer circumferential surface 315b of piercing section 314b is referred to as "similar shape portion". The similar shape portion corresponds to the region of inner wall surface 305 indicated by a reference numerical 308. In the example shown in FIG. 4B, similar shape portion 308 corresponds to ¾ or 75% of the total length of outer circumferential surface 315b of piercing section 314b. But, 75% of the total length is not necessarily required for the length of similar shape portion 308. An area of inner wall surface 305 along one face of outer circumferential surface 315b is sufficient. That is, in this case, the length of the similar shape portion 308 is ¼ or 25% of outer circumferential surface 315b. Thus, similar shape portion 308 may only have a length corresponding to not less than 25% of the length (perimeter) of outer circumferential surface 315b. This applies to the relationship between cylindrical piercing section 314a and inner wall surface 306. More specifically, the similar shape portion (not shown) of inner wall surface 306 may only have a length corresponding to at least ¼ of outer circumferential surface 315a of cylindrical piercing section 314a.

Because of the reason described above, a narrower gap between outer circumferential surface 315b and inner wall surface 305 in FIG. 4B results in more reliable shearing by piercing section 314b. Accordingly, if the size from the center "c" of the piercing section to outer circumferential surface 315b is assumed to be "b" and the shortest distance from inner wall surface 305 to the center "c" of the piercing section is assumed to be "a", the shortest distance (a-b) from inner wall surface 305 of the opening section to outer circumferential surface 315b of piercing section 314b should be not greater than ½ and more preferably ⅓ of the shortest distance "a" from inner wall surface 305 to the center "c" of the piercing section 314b.

Figure 5:
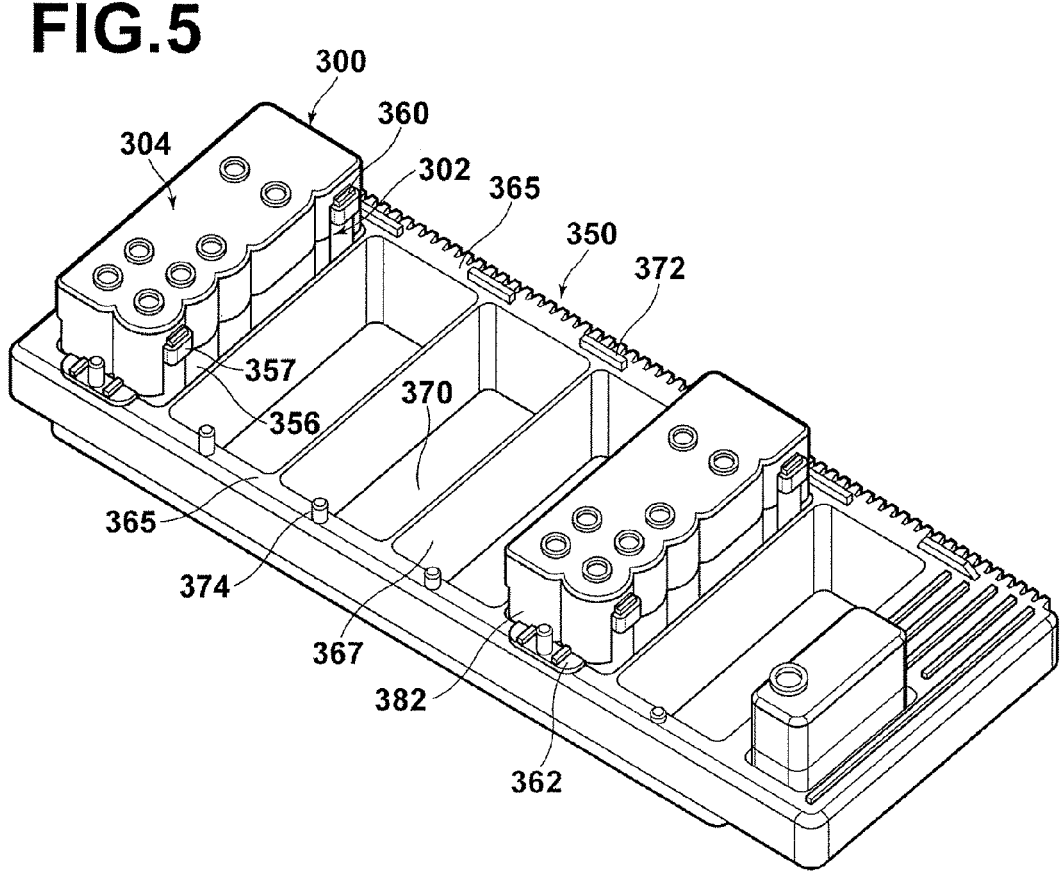
FIG. 5 is a perspective view in which the reagent container shown in FIG. 4A is disposed in a reagent container mounting area of an analyzing device.

Next, the features of the second embodiment will be further described with reference also to FIG. 5. FIG. 5 is a perspective view in which reagent container 300 is disposed in a reagent container mounting area 350 of an analyzing device (not shown). Container body 302 of reagent container 300 has two upward engaging recesses 357 formed on outer circumferential wall 356. Lid 304 has downward engaging protrusions (engaging section) 360 formed at positions corresponding to engaging recesses 357 to engage with and held by engaging recesses 357. This allows integrated reagent container 300 to be formed by pressing lid 304 onto container body 302 and causing them to engage with each other. Horizontally protruding tabs (positioning section) 362 and 363 (FIG. 4A) are formed on the wall surfaces of cover wall 382 of lid 304 oppositely separated from each other in a longitudinal direction of cover wall 382. Tab 362 has a hole 362a formed in the center (FIG. 4A).

In the mean time, reagent container mounting area 350 has a ladder-like shape as shown in FIG. 5. Reagent container mounting area 350 includes a plurality of compartments 370 for mounting reagent containers 300 formed in a row by partition plates provided between left and light rails 365. One of rails 365 has protrusions 374 corresponding to each hole 362a of reagent container 300 described above, formed at the positions corresponding to compartment 370. The other rail 365 has protruding bars 372, spaced apart from each other, formed at the positions corresponding to respective compartments 370. Protrusions 374 and protruding bars 372 are referred to as "members on the side of the analyzing device". When reagent container 300 is mounted in reagent container mounting area 350, protrusion 374 engages with hole 362a of tab 362 described above and protruding bar 372 is located on each side of tab 363 to prevent the movement of the tab, whereby reagent container is positioned reliably.

As shown in FIG. 4A, in container body 302 of reagent container 300 of the second embodiment, one of the portions of outer circumferential wall 356 along a longitudinal direction of the body has a plurality of vertically extending concavo-convex shapes, while the other portion is relatively flat. The reason is to equalize the wall thicknesses of holding sections 302a, 302b, 302c, 302d, 302e, 302f, and 302g of container body 302. The wall thickness equalization may prevent appearance quality degradations and capacity changes in holding sections 302a, 302b, 302c, 302d, 302e, 302f, and 302g due to shrinkage. Further, the wall thickness equalization does not affect the engagement of engaging protrusions 360 with engaging recesses 357 or labeling on container body 302. Cover wall 382 of lid 304 also has concavo-convex shapes formed thereon corresponding to the concavo-convex shapes described above. When putting lid 304 on container body 302, the concavo-convex shapes of container body 302 may serve as a guide for inner wall surface 383 of lid 304. Further, the concavo-convex shapes are formed only on one side wall so that erroneous capping of lid 304 on container body 302 in an opposite manner may also be prevented.

Figure 6A:
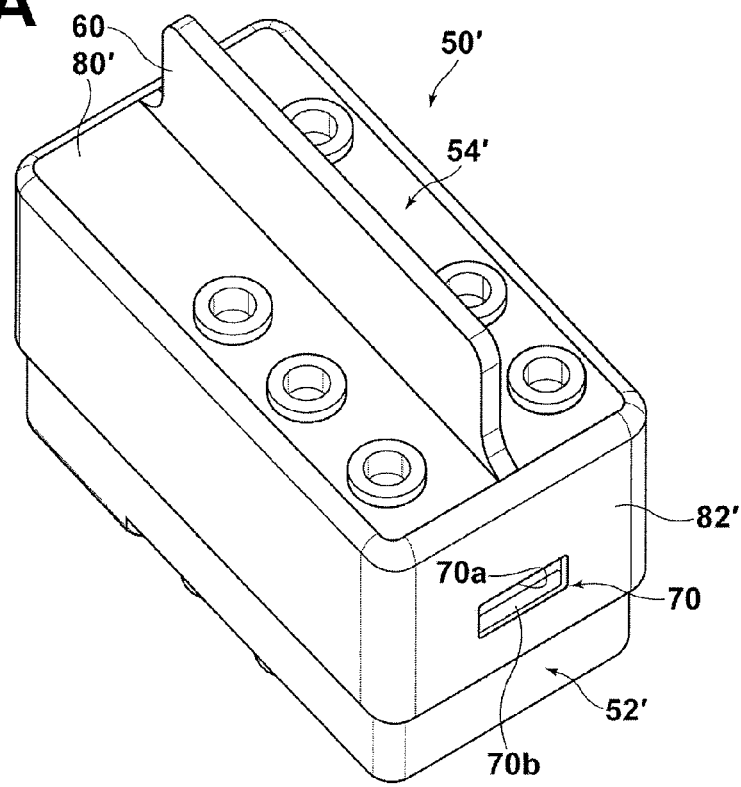
FIG. 6A is a perspective view of a first modification of the reagent container shown in FIG. 2.
Figure 6B:
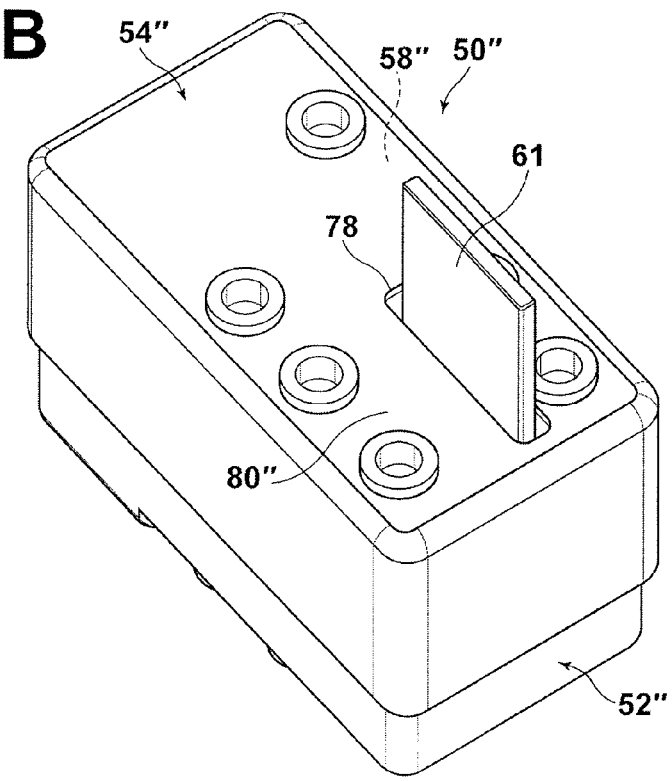
FIG. 6B is a perspective view of a second modification of the reagent container shown in FIG. 2.

Next, modifications of reagent container 50 will be described with reference to FIGS. 6A and 6B. FIG. 6A is a perspective view of a first modification, and FIG. 6B is a perspective view of a second modification. Reagent container 50' shown in FIG. 6A has container body 52', which is identical to container body 52 of the first embodiment, and lid 54', which is different from lid 54 of the first embodiment in that it has handle 60. Handle 60 is formed on upper wall 80' of lid 54' along a longitudinal direction of upper wall 80' as a plate-like protrusion protruding perpendicularly with respect to upper wall 80'. Handle 60 extends substantially the entirety of upper wall 80' in a longitudinal direction along substantially the center of the width of upper wall 80'. Handle 60 has a protrusion height that allows a person to pinch it with fingers.

As in the first embodiment, when using lid 54', lid 54' is put on container body 52' from above and simply pressed downward. Then, reagent container 50' can be carried around by pinching the handle so that reagent container 50' may be mounted easily in an analyzing device or the like. When lid 54' is provided with handle 60 as in the present modification, rectangular engaging opening (engaging section) 70a is provided in cover wall 82' and engaging protrusion 70b that makes concavo-convex engagement with engaging opening 70a is provided on container body 52' so that container body 52' is securely held by lid 54'. A pair of engaging opening 70a and engaging protrusion 70b is provided at each of opposite positions of cover wall 82'. But the shapes and attaching positions of engaging opening 70a and engaging protrusion 70b are not limited to those described in the first modification, and modifications and changes may be made. It should also be appreciated that the shape, size (length and height), and attaching position of handle 60 can be changed.

Next, reagent container 50" of second modification shown in FIG. 6B differs from the first modification in that handle 61 is provided to container body 52" and not to lid 54". Handle 61 is integrally formed with top wall 58" of container body 52" along a longitudinal direction of top wall 58" as a plate-like protrusion protruding perpendicularly with respect to top wall 58". The length of handle 61, i.e., the length thereof along the longitudinal direction of top wall 58" is about ⅓ of the size of the top wall 58" in the longitudinal direction thereof. The attaching position of handle 61 is adjacent to one of the ends of container body 52" in the longitudinal direction of container body 52". Handle 61 has a protrusion height that allows a person to pinch it with fingers. In the mean time, slot or clearance hole 78 having a size sufficient to pass through handle 61 is formed in upper wall 80" of lid 54" at the position corresponding to handle 61. When attaching lid 54" to container body 52", lid 54" may simply be pressed downward, as in the first modification. In the case of the second modification, handle 61 is formed to protrude from container body 52" so that container body 52" is secured from dropping even if it is heavy. Therefore, second modification does not require the arrangement of engaging opening 70a and engaging protrusion 70b of reagent container 50' of the first modification.

Further, the shape, size (length and height), and attaching position of handle 61 can be changed.

Figure 7:
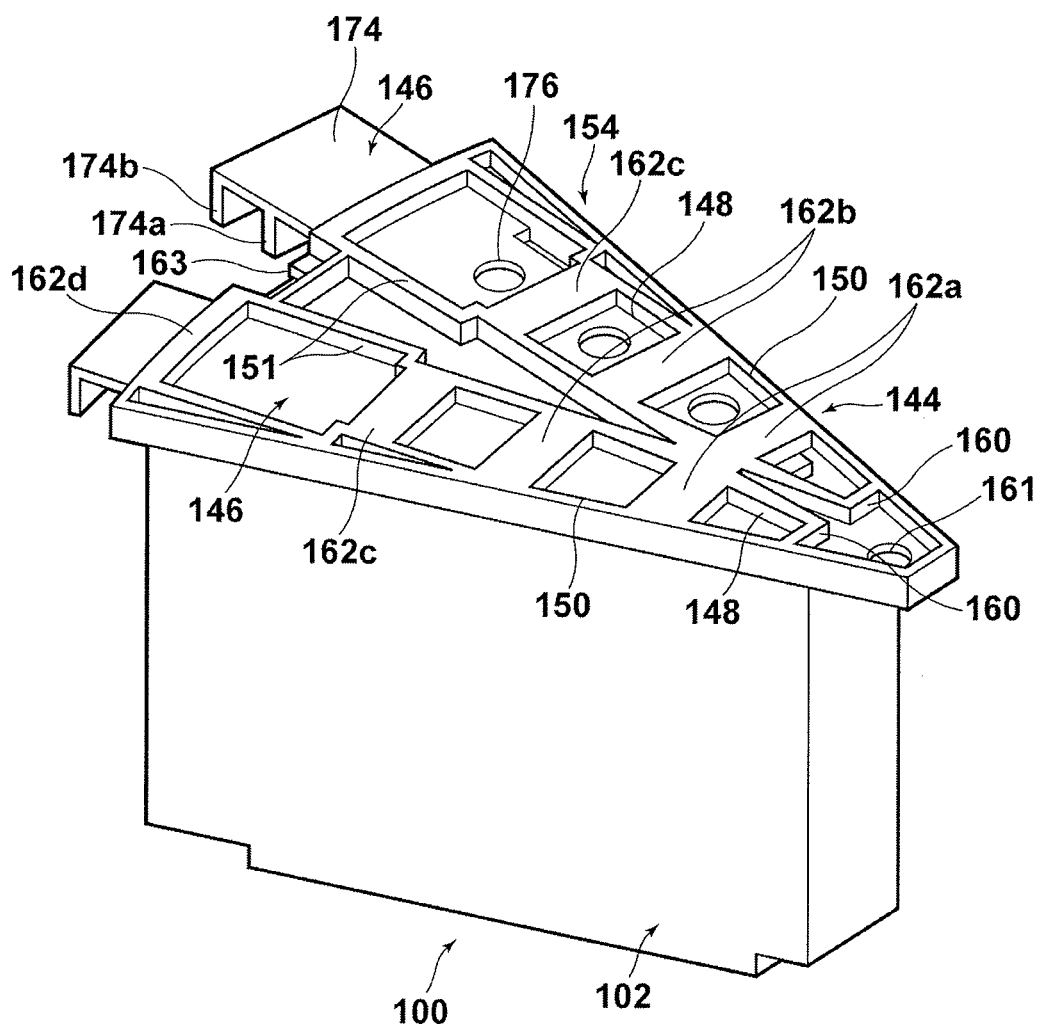
FIG. 7 is an overall perspective view of a reagent container according to a third embodiment of the present invention.
Figure 8:
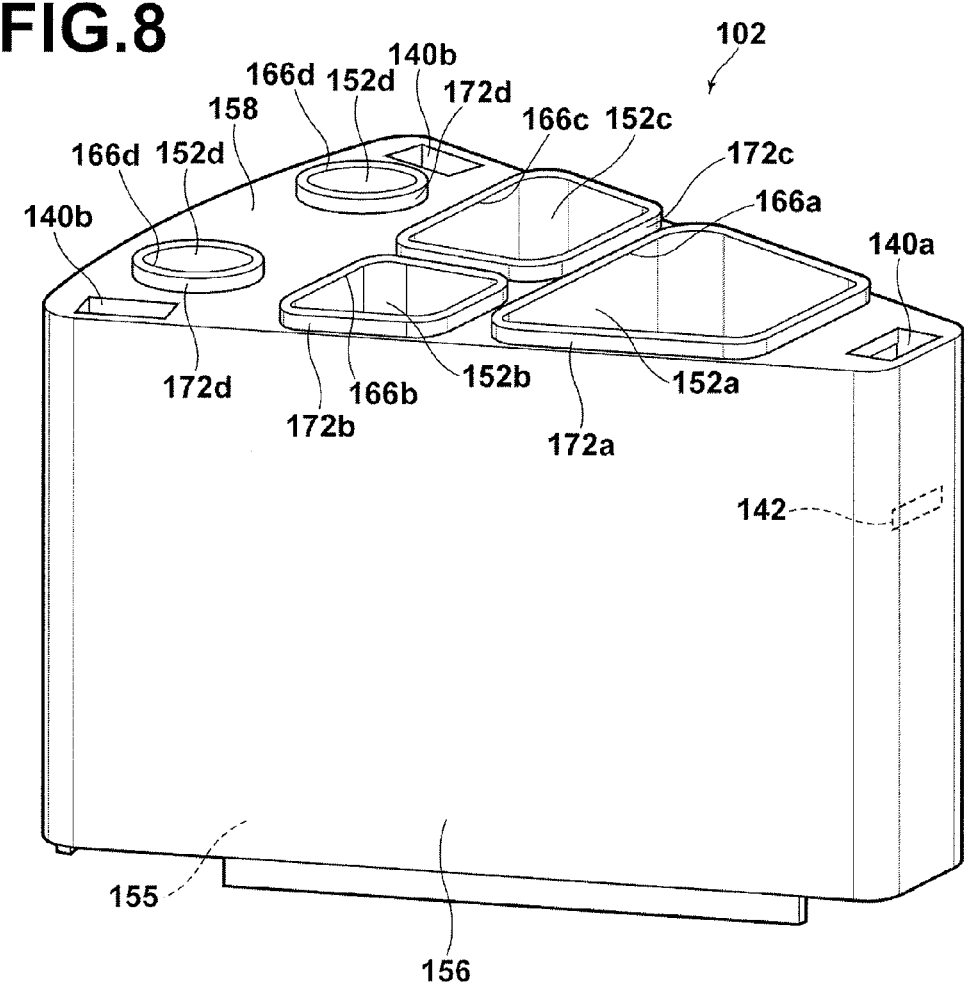
FIG. 8 is a perspective view of the container body of the reagent container shown in FIG. 7.

Next, reagent container 100 according to a third embodiment of the present invention will be described with reference to FIGS. 7 and 8. FIG. 7 is an overall perspective view of reagent container 100. FIG. 8 is a perspective view of container body 102 of reagent container 100. Container body 102 has a fan shape in planar view and a rectangular shape in side view. Such shape is appropriate for mounting reagent containers 100 in an analyzing device side by side in a circle with the narrower portion of the fan shape of each reagent container 100 being oriented on the inner side. For the sake of convenience for explanation, hereinafter, the narrower portion is referred to as "first end" and the arc shaped wider side is referred to as "second end".

As shown in FIG. 8, container body 102 includes a plurality of holding sections 152*a*, 152*b*, 152*c*, and 152*d* having openings (opening sections) 166 (166*a*, 166*b*, 166*c*, and 166*d*) in top wall 158. Holding sections 152*a*, 152*b*, 152*c*, and 152*d* are integrally formed with top wall 158 and hang down perpendicularly in the internal space 155 formed by outer circumferential wall 156 from top wall 158, as in the first embodiment. Opening 166*a* on the first end side has a large trapezoidal shape and opening 166*d* on the second end side has a circular shape. Openings 166*b* and 166*c* located intermediate between the first and second ends have trapezoidal shapes smaller than that of opening 166*a*. Ribs 172*a*, 172*b*, 172*c*, and 172*d* are formed around openings 166*a*, 166*b*, 166*c*, and 166*d* respectively, as in the first embodiment. Further, openings 166*a*, 166*b*, 166*c*, and 166*d* are covered with a seal member before being put into practical use as in the previous embodiments. Mounting holes 140 (140*a* and 140*b*) for mounting legs 190 (FIG. 9) of lid 154, to be described later, are formed in top wall 158 at three corners of container body 102. Engaging section 142 that engages with amounted leg is formed inside of each of mounting holes 140*a* and 140*b*.

Figure 9:
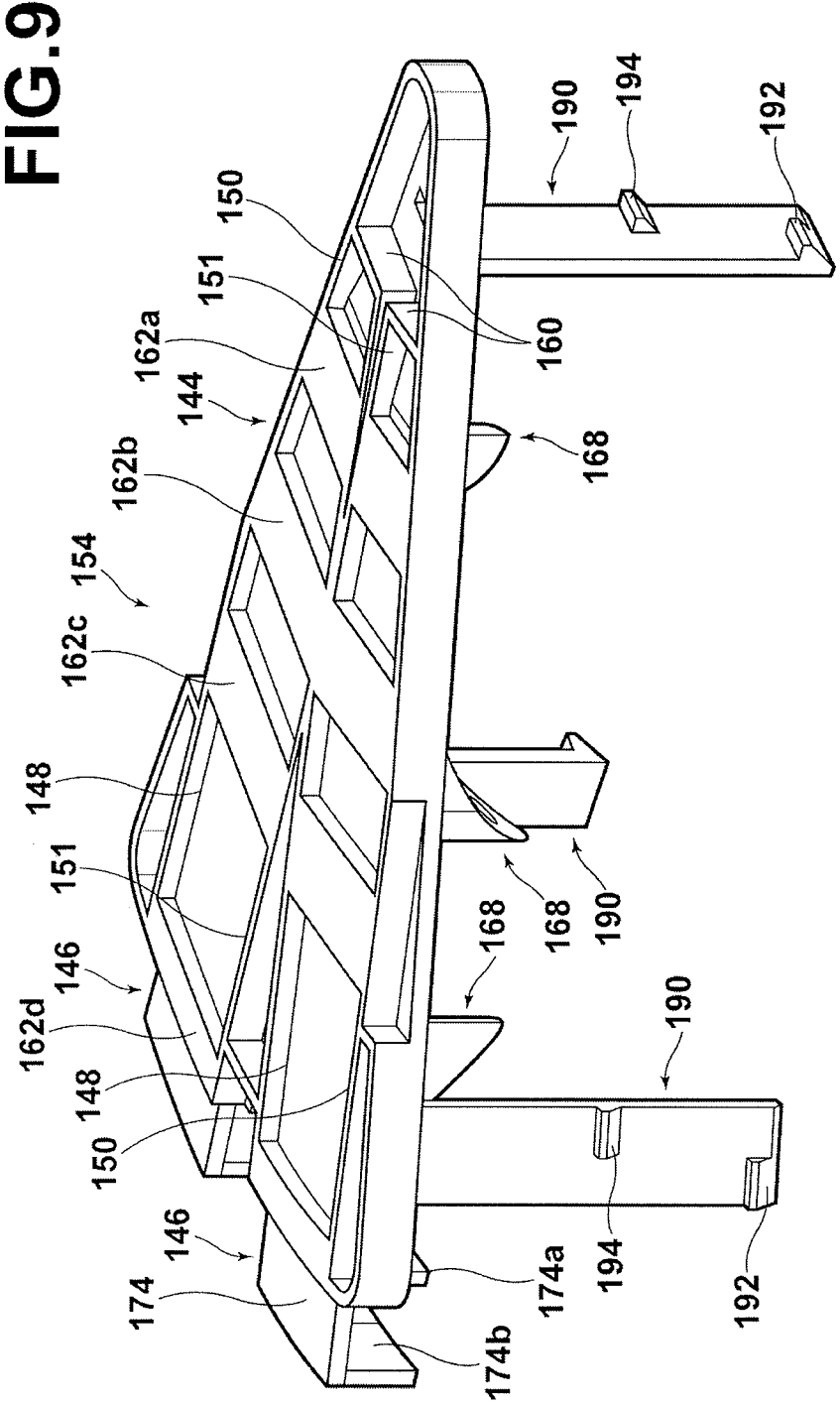
FIG. 9 is a perspective view of the lid to be mounted on the upper side of the container body shown in FIG. 8.
Figure 10:
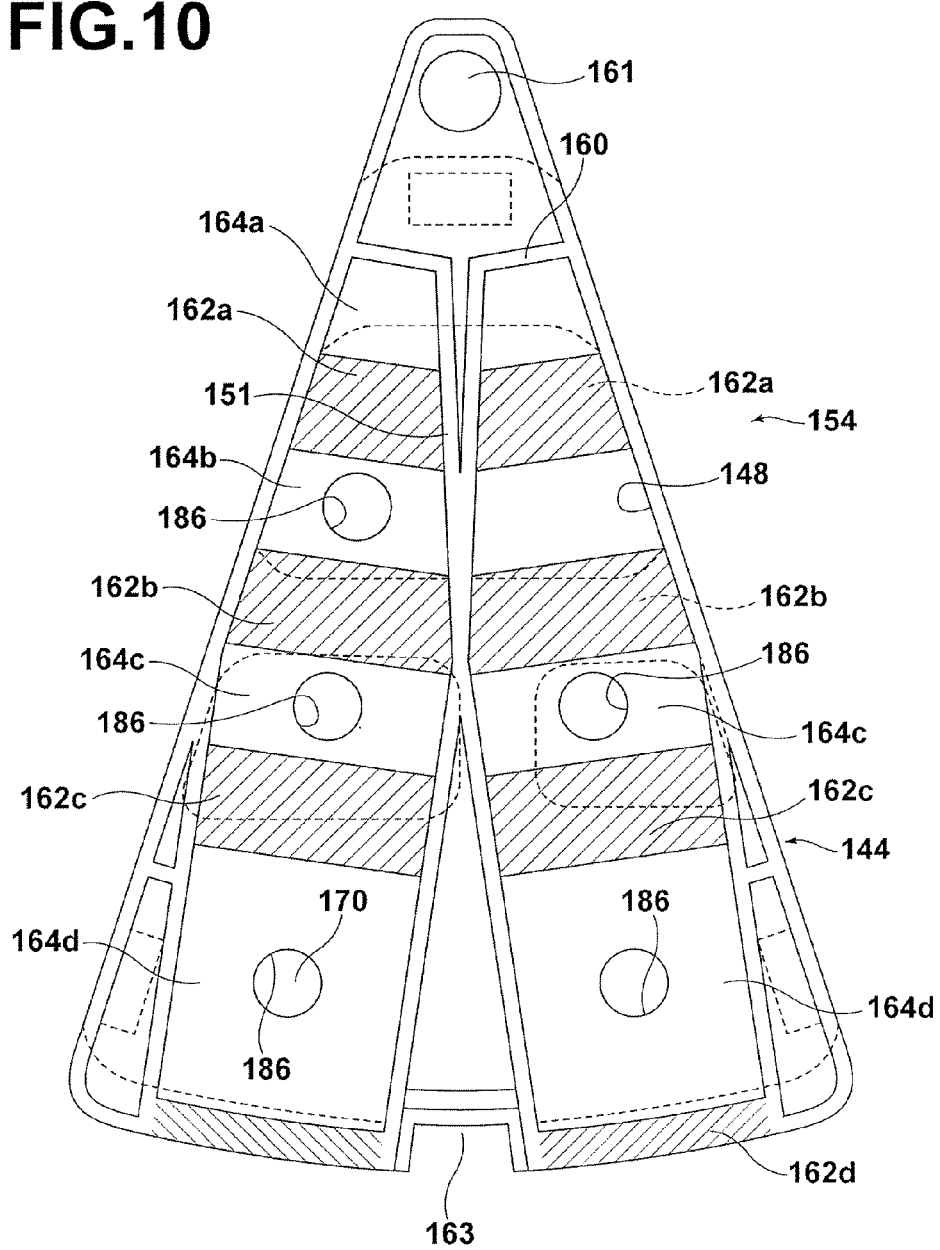
FIG. 10 is a plane view of a main body member of the lid without sliding plates (shutters).

Next, lid 154 will be described with reference also to FIGS. 9 and 10. FIG. 9 is a perspective view of main body member 144 of lid 154 to be mounted on the upper side of container body 102. FIG. 10 is a plane view of lid 154 removed of a sliding plate (shutter) 146. Lid 154 include main body member 144 to be placed on the upper side of container body 102 and two sliding plates 146 slidably mounted in main body member 144. In overview, main body member 144 has a fan-like or triangular shape similar to that of the upper side of container body 102 with two channels 148 formed therein for slidably receiving sliding plates 146. Channels 148 are formed by guide walls 150 formed substantially along the outer edges of main body member 144 in a longitudinal direction thereof and a pair of guide walls 151 formed between the pair of guide walls 150. Each guide wall 150 and each guide wall 151 is terminated at end wall 160 on the first end side.

Upper end of guide walls 150 and 151 are integrally formed with connection walls 162 (162*a*, 162*b*, 162*c*, and 162*d*) at positions spaced apart from each other from the first end side to the second end side. In FIG. 10, connection walls 162 (162*a*, 162*b*, 162*c*, and 162*d*) on the upper end side are indicated by hatched lines for clarity. In the mean time, other connection walls 164 (164*a*, 164*b*, 164*c*, and 164*d*) (FIG. 10) are formed between end wall 160 and connection wall 162*a* and between connection walls (162*a*, 162*b*, 162*c*, and 162*d*) on the opposite side of connection walls 162, i.e., on the lower end side of guide walls 150 and 151. In FIG. 9, connection walls 164 (164*a*, 164*b*, 164*c*, and 164*d*) are not seen because they are located under sliding plates 146. Not shown gaps for passing sliding plates 146 are formed between connection walls 162 and connection walls 164, i.e., between connection walls 162 and connection walls 164 in a direction perpendicular to sliding plates 146. Consequently, sliding plates 146 can slide within channels 148 guided by guide walls 150, 151 and connection walls 162, 164.

As shown in FIG. 10, a plurality of circular opening 186, corresponding to openings 86 of lid 54 in the first embodiment, is formed in connection walls 164*c* and 164*d* which lie on the side closer to container body 102. Further, another opening 186 is formed in one of connection walls 164*b*. Openings 186 are formed at positions corresponding to openings 166 of holding sections 152*a*, 152*b*, 152*c*, and 152*d* of container body 102 shown in FIG. 8. Piercing sections 168 (FIG. 9) having passages 170 in communication with openings 186 are formed under openings 186. Piercing sections 168 have the same outside dimension in plane view and the lower ends thereof have an inclined shape, as in the previous embodiments.

Figure 11:
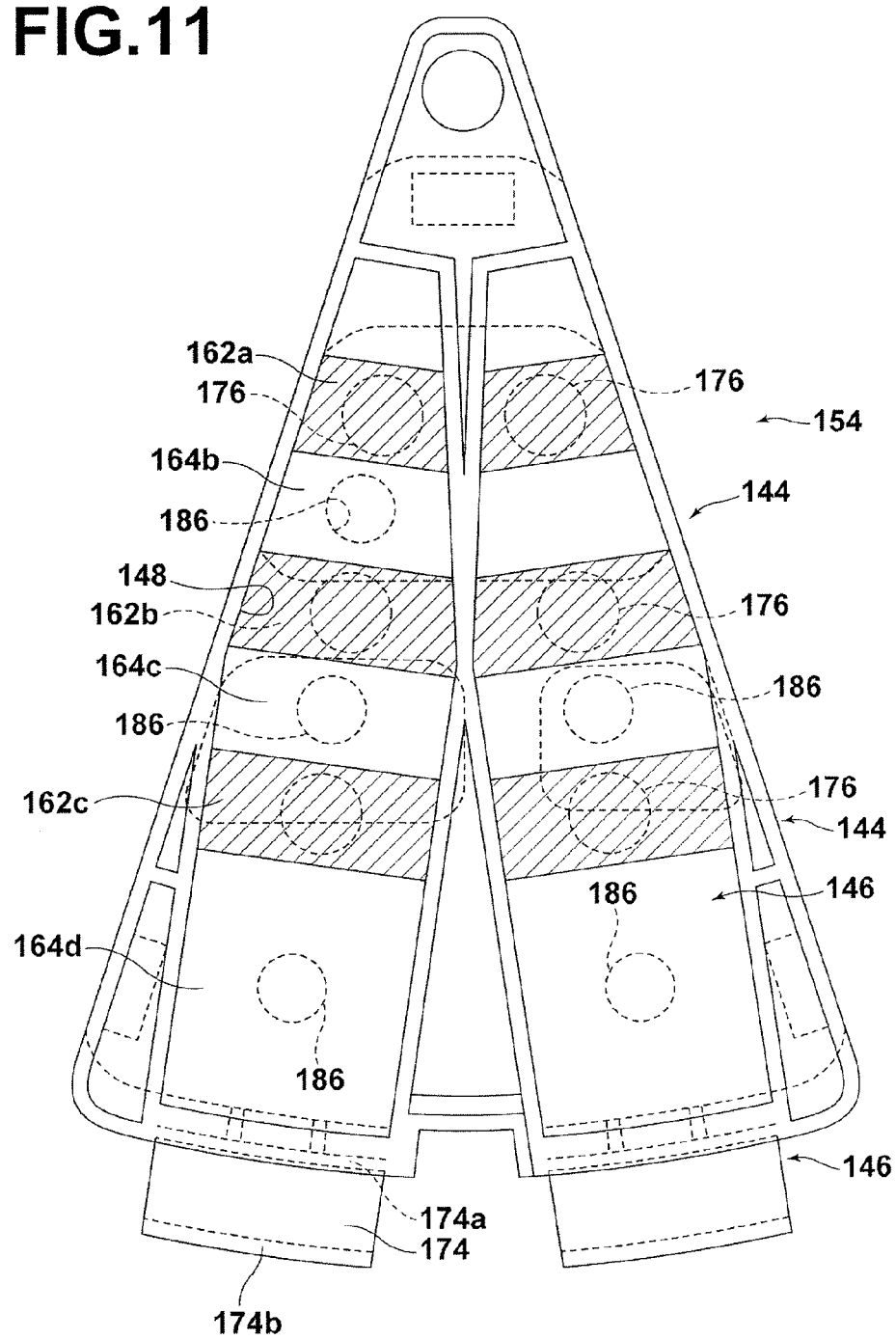
FIG. 11 is a plane view of the lid shown in FIG. 10, illustrating the state in which the sliding plates are mounted in the main body member shown in FIG. 10.

Sliding plates 146 will now be described with reference also to FIG. 11. FIG. 11 is a plane view of lid 154, illustrating the state in which sliding plates 146 are mounted in main body member 144 shown in FIG. 10. Two sliding plates 146 are identical and have an outer shape, in plane view, which is complementary to the shape of channel 148 in plane view formed by guide walls 150 and 151. Sliding plate 146 has extended portion 174 protruding from channel 148 to the outside on the second end side. Each extended portion 174 has two plate pieces 174*a* and 174*b* hanging down perpendicularly from the plate surface of sliding plate 146. A member that engages with plate pieces 174*a* and 174*b*, to be described later, moves in between plate pieces 174*a* and 174*b* from automatic analyzing device 400 (FIG. 12), whereby slide plates 146 are pushed inside of channels 148 or pulled out therefrom.

As shown in FIG. 11, openings 186 described above are normally covered with sliding plates 146. Each of sliding plates 146, at the position shown in FIG. 11, has holes 176 formed therein which are slightly larger than openings 186 at the same positions as connection walls 162*a*, 162*b*, and 162*c*. One of holes 176 is aligned with one of openings 186 of any one of holding sections 152 depending on the pulled out amount of each of sliding plates 146. That is, alignment of one of openings 186 with one of holes 176 allows probe 6 to be inserted. FIG. 7 depicts holes 176 formed in one of pulled out sliding plates 146. When reagent container 100 is not used, sliding plates 146 are pushed inside as shown in FIG. 11, whereby openings 186 are closed and reagents can be prevented from being exposed to ambient air.

Now referring again to FIG. 9, structures for attaching lid 154 to container body 102 will be described. Lid 154 has leg 190*a* on the first end side and legs 190*b* at the corners on the second end side integrally formed therewith so as to extend downward. Legs 190*a* and 190*b* are, hereinafter, collectively referred to as legs 190. Legs 190 are formed at positions corresponding to mounting holes 140 of container body 102. Each of legs 190 has two outwardly oriented locking protrusions (engaging sections) 192 and 194 formed spaced apart from each other in a longitudinal direction of the leg. Locking protrusion 192 is formed at the bottom end portion and one of the side end portions of leg 190, while locking protrusion 194 is formed at substantially the central portion in a length direction and the other side end portion of leg 190. Locking protrusion 192 engages with engaging section 142 of container body 102 described above and temporarily fixed (temporarily locked). When lid 154 is pressed down to open the holding sections, locking protrusions 194 of legs 190 engage with engaging sections 142 and lid 154 is locked (main locking) to container body 102. At this time, piercing sections 168 pierce the seal member covering each of openings 166.

The locking structure of leg 190 is not limited to that of the aforementioned embodiment. For example, locking protrusion 192 at the tip (bottom end) of leg 190 is not necessarily required; and it may simply function as a tongue for guiding the leg to the inside of mounting hole 140. Alternatively, a configuration may be adopted in which one locking protrusion is provided with two engaging sections at positions inside of mounting hole 140 corresponding to temporary locking and main locking. The structure of leg 190 that can take the positions of temporary locking and main locking can be applied to block-like reagent containers 50 and 300.

It is noted that positioning hole 161 is formed on the first end side and notch 163 is formed in the center on the second end side. These are used for positioning reagent container 100 when mounted in an analyzing device and collectively referred to as positioning sections. The mounting mode will now be described with reference to FIG. 12. FIG. 12 is a perspective view in which reagent container 100 is mounted in analyzing device 400. Compartments 404 having a shape complementary to that of reagent container 100 are radially formed around axis 406 in reagent storage 402 of analyzing device 400. In each compartment 404, pin 408 is protrudingly formed on the inner side and tongue 410 is protrudingly formed on the outer side in the radial direction. Pin 408 and tongue 410 are referred to as automatic analyzing device 400 side members. When reagent container 100 is placed in compartment 404, positioning hole 161 engages with pin 408 and tongue 410 engages with notch 163 of lid 154 of reagent container 100, whereby the position of reagent container 100 is fixed inside of reagent storage 402. The important fact here is that the lid 154 engages with pin 408 and tongue 410 of reagent storage 402. This ensures that the positions of holes 176 of lid 154 and probe 6 are aligned.

So far, embodiments of the present invention have been described in detail, but it should be appreciated that the present invention is not limited to the embodiments described above and various modifications and changes may be made. The similarity relationship between piercing sections 314 and portions of inner wall surfaces 305 and 306 of holding sections 302a and 302b described in the second embodiment is not limited to the second embodiment, and can be applied to each of the embodiments and modifications described above.

What is claimed is:

1. A reagent container, comprising:
a container body having a plurality of holding sections respectively having a openings therein each defined by opposing walls, each holding a reagent and into which a probe of an automatic analyzing device is inserted to suck the reagent, with an opening of each of the holding sections sealed with at least one sheet-like seal member; and
a lid having a plurality of open ended hollow piercing sections, formed on a lower surface of the lid, protruding downward for piercing the seal member at each of the openings, and allowing the probe to be inserted therethrough or withdrawn therefrom, the piercing sections having, as the maximum outer size thereof, a size of less than or equal to ½ the maximum distance between opposed inner surfaces of the opposing walls of at least one of the holding sections, each of the piercing sections having a shape for shearing the seal member, at a lower end thereof,
wherein the reagent container is configured such that the seal member is pierced by pressing the lid onto the container body from above and the probe is allowed to be inserted into the holding sections through hollow sections of the piercing sections, and
wherein when pressing is conducted by the lid, the piercing sections are dispose at a position with respect to the opening where the shortest distance from an inner wall surface of the corresponding opening of the container body to an outer circumferential surface of the piercing section is not greater than ½ of the shortest distance from the inner wall surface to the center of the piercing section.

2. The reagent container of claim 1, wherein the reagents comprise a plurality of types of reagents and each of the holding sections holds an amount of each of the corresponding reagents according to a required amount thereof.

3. The reagent container of claim 2, wherein at least one of the openings of the plurality of holding sections has a size different from the size of the rest of the openings and each of the piercing sections has the same outer dimension.

4. The reagent container of claim 3, wherein the seal member is made of a material that adheres tightly to the piercing sections of the lid after pierced.

5. The reagent container of claim 4, wherein the seal member is made of a material that does not produce a fragment separated from the seal member when piercing is performed by the piercing sections.

6. The reagent container of claim 5, wherein at least one of the plurality of piercing sections has a protruding length protruding downward from the lower surface of the lid different from the protruding length of the rest of the piercing sections, whereby the piercing sections are configured to pierce the seal member in a stepwise manner.

7. The reagent container of claim 6, wherein the lid comprises an engaging section that engages with the container body to hold the lid at a position above the container body where the piercing sections do not interfere with the seal member.

8. The reagent container of claim 7, wherein the container body has an outer circumferential wall, and the lid comprises a cover wall whose inner wall surface is guided by the outer circumferential wall when the lid is pressed onto the container body from above and an upper wall having the piercing sections on a lower surface thereof.

9. The reagent container of claim 8, wherein the lid comprises a positioning section that engages with a member on the side of the automatic analyzing device so as to be fixedly positioned.

10. The reagent container of claim 9, wherein a handle is provided on the outside of the reagent container.

11. The reagent container of claim 1, wherein at least one of the openings of the container body has a similar shape portion along an outer circumferential surface of the corresponding piercing section and the length of the similar shape portion along the outer circumferential surface is not less than 25% of the length of the outer circumferential surface.

12. The reagent container of claim 1, wherein at least one of the openings of the plurality of holding sections has a size different from the size of the rest of the openings and each of the piercing sections has the same outer dimension.

13. The reagent container of claim 1, wherein the seal member is made of a material that adheres tightly to the piercing sections of the lid after pierced.

14. The reagent container of claim 1, wherein the seal member is made of a material that does not produce a fragment separated from the seal member when piercing is performed by the piercing sections.

15. The reagent container of claim 1, wherein at least one of the plurality of piercing sections has a protruding length protruding downward from the lower surface of the lid different from the protruding length of the rest of the piercing sections, whereby the piercing sections are configured to pierce the seal member in a stepwise manner.

16. The reagent container of claim 1, wherein a handle is provided on the outside of the reagent container.

17. The reagent container of claim 1, wherein the lid comprises an engaging section that engages with the container body to hold the lid at a position above the container body where the piercing sections do not interfere with the seal member.

18. The reagent container of claim 1, wherein the container body has an outer circumferential wall, and the lid comprises a cover wall whose inner wall surface is guided by the outer circumferential wall when the lid is pressed onto the container body from above and an upper wall having the piercing sections on a lower surface thereof.

19. The reagent container of claim 1, wherein the lid comprises a positioning section that engages with a member on the side of the automatic analyzing device so as to be fixedly positioned.

20. The reagent container of claim 1, wherein the each lower end of the each piercing sections having the shape for shearing the seal member is disposed so he that a tip of teach lower end is located at a position, in the lower end, which is closest to an outside of the lid.

21. The reagent container of claim 1, wherein a planer shape of the lid forms along side and a short side, and a tip of the generally rectangular shape having a l each lower end is located at a position, in the lower end, which is closest to an outside in the direction orthogonal to the longitudinal direction of the lid.

* * * * *